US011268971B2

(12) United States Patent
Makino et al.

(10) Patent No.: US 11,268,971 B2
(45) Date of Patent: Mar. 8, 2022

(54) AUTOMATED ANALYZER

(71) Applicant: HITACHI HIGH-TECHNOLOGIES CORPORATION, Tokyo (JP)

(72) Inventors: Akihisa Makino, Tokyo (JP); Masashi Akutsu, Tokyo (JP); Hiroyuki Mishima, Tokyo (JP); Akihiro Yasui, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 16/476,884

(22) PCT Filed: Jan. 31, 2018

(86) PCT No.: PCT/JP2018/003253
§ 371 (c)(1),
(2) Date: Jul. 10, 2019

(87) PCT Pub. No.: WO2018/163674
PCT Pub. Date: Sep. 13, 2018

(65) Prior Publication Data
US 2020/0264201 A1  Aug. 20, 2020

(30) Foreign Application Priority Data
Mar. 7, 2017  (JP) .............................. JP2017-043034

(51) Int. Cl.
*G01N 35/00* (2006.01)
*G01N 35/02* (2006.01)
(Continued)

(52) U.S. Cl.
CPC ....... *G01N 35/0095* (2013.01); *G01N 35/026* (2013.01); *A61B 5/00* (2013.01);
(Continued)

(58) Field of Classification Search
CPC .. G01N 35/0095; G01N 35/026; G01N 35/00; G01N 35/02; G01N 35/04;
(Continued)

(56) References Cited

U.S. PATENT DOCUMENTS 6,080,364 A * 6/2000 Mimura ........... G01N 35/00712
422/63
6,521,183 B1   2/2003 Burri et al.
(Continued)

FOREIGN PATENT DOCUMENTS

CN   102650644 A   8/2012
CN   105229473 A   1/2016
(Continued)

OTHER PUBLICATIONS

International Preliminary Report on Patentability received in corresponding International Application No. PCT/JP2018/003253 dated Sep. 19, 2019.
(Continued)

*Primary Examiner* — Benjamin R Whatley
*Assistant Examiner* — Curtis A Thompson
(74) *Attorney, Agent, or Firm* — Mattingly & Malur, PC

(57) ABSTRACT

An automated analyzer is provided with one or more dispensing lines 109, 209 that are each for loading and unloading, at one end thereof, a sample rack 101 having placed therein one or more sample containers accommodating a sample for analysis and for conveying the sample rack back and forth from a dispensing position for dispensing the sample from the sample containers and sample rack removal parts 111, 211 that are provided adjacent to the other ends of the dispensing lines 109, 209 and provide and receive sample racks to and from the dispensing lines 109, 209. According to this configuration, it is possible to convey an
(Continued)

urgent sample while suppressing device complexity, preventing cost from increasing, and also maintaining speed.

2 Claims, 11 Drawing Sheets

(51) Int. Cl.
| | |
|---|---|
| A61B 5/00 | (2006.01) |
| G01F 23/00 | (2022.01) |
| G01N 1/22 | (2006.01) |
| G01N 21/00 | (2006.01) |
| G01N 33/48 | (2006.01) |
| G01N 35/04 | (2006.01) |
| G01N 35/10 | (2006.01) |

(52) U.S. Cl.
CPC ............... *G01F 23/00* (2013.01); *G01N 1/22* (2013.01); *G01N 21/00* (2013.01); *G01N 33/48* (2013.01); *G01N 35/00* (2013.01); *G01N 35/02* (2013.01); *G01N 35/04* (2013.01); *G01N 35/10* (2013.01); *G01N 35/1065* (2013.01); *G01N 2035/0496* (2013.01); *G01N 2035/1051* (2013.01)

(58) Field of Classification Search
CPC .................. G01N 21/00; G01N 33/48; G01N 2035/0496; G01N 35/1065; G01N 35/10; G01N 2035/1051; G01N 1/22; A61B 5/00; G01F 23/00
See application file for complete search history.

(56) References Cited

U.S. PATENT DOCUMENTS

| | | | | |
|---|---|---|---|---|
| 7,842,237 | B1* | 11/2010 | Shibuya | ............... G01N 35/026 422/64 |
| 2004/0186360 | A1* | 9/2004 | Suzuki | ................. G01N 35/026 600/310 |
| 2008/0056944 | A1* | 3/2008 | Nakamura | ....... G01N 35/00712 422/67 |
| 2011/0200485 | A1* | 8/2011 | Akutsu | ............ G01N 35/00712 422/67 |
| 2011/0256022 | A1* | 10/2011 | Akutsu | ............ G01N 35/00603 422/65 |
| 2011/0271773 | A1* | 11/2011 | Komatsu | ............ G01N 35/0092 73/863.01 |
| 2012/0216610 | A1 | 8/2012 | Kanayama | |
| 2014/0170023 | A1* | 6/2014 | Saito | ...................... G01N 35/04 422/65 |
| 2016/0124010 | A1* | 5/2016 | Makino | ................. G01N 35/026 422/65 |
| 2017/0192027 | A1 | 7/2017 | Makino et al. | |

FOREIGN PATENT DOCUMENTS

| | | | | | |
|---|---|---|---|---|---|
| JP | 9-274046 | A | | 10/1997 | |
| JP | 2003-262642 | A | | 9/2003 | |
| JP | 2003262642 | A | * | 9/2003 | |
| JP | 2004-279357 | A | | 10/2004 | |
| JP | 2008-122421 | A | | 5/2008 | |
| JP | 2008122421 | A | * | 5/2008 | .............. G01N 35/02 |
| JP | 2008-281453 | A | | 11/2008 | |
| JP | 2010-197048 | A | | 9/2010 | |
| JP | 2011-2340 | A | | 1/2011 | |
| JP | 2011002340 | A | * | 1/2011 | |
| JP | 2016-048255 | A | | 4/2016 | |

OTHER PUBLICATIONS

Chinese Office Action received in corresponding Chinese Application No. 201880013523.6 dated Dec. 19, 2019.

International Search Report of PCT/JP2018/003253 dated Apr. 10, 2018.

Extended European Search Report received in corresponding European Application No. 18764008.1 dated Dec. 2, 2020.

* cited by examiner

[FIG. 1]
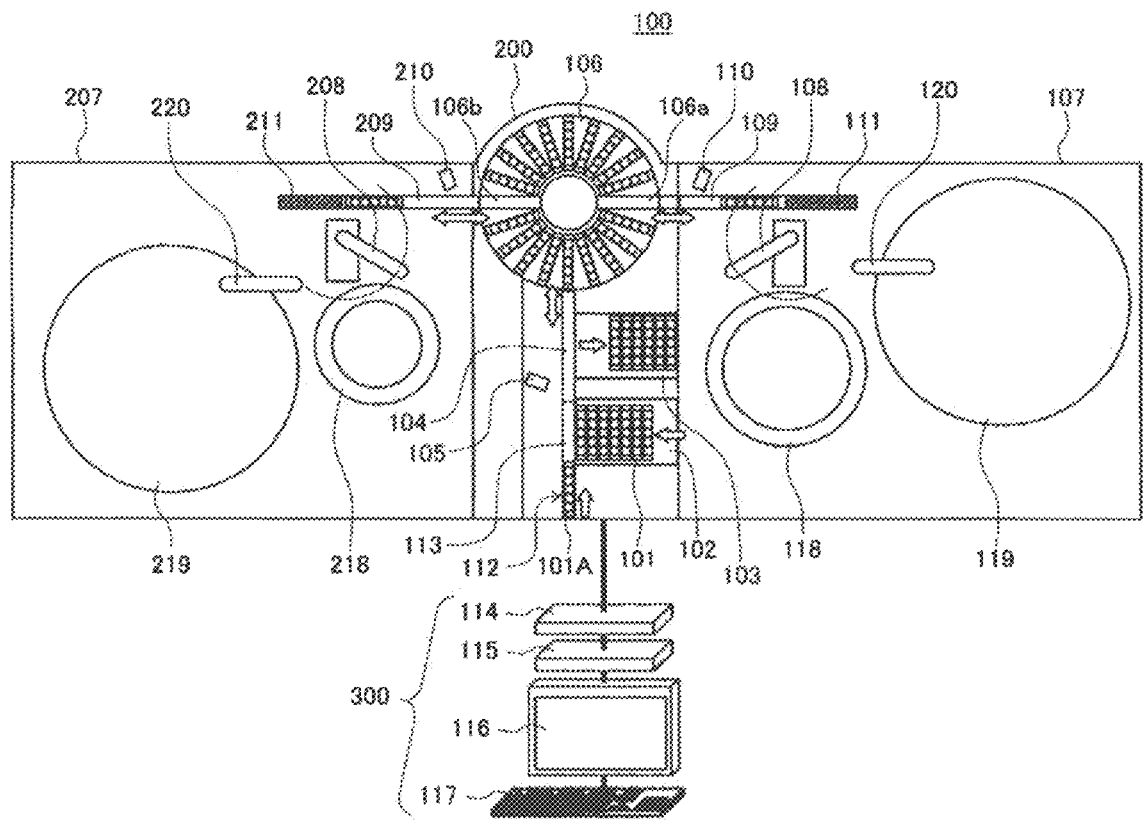
[FIG. 2]
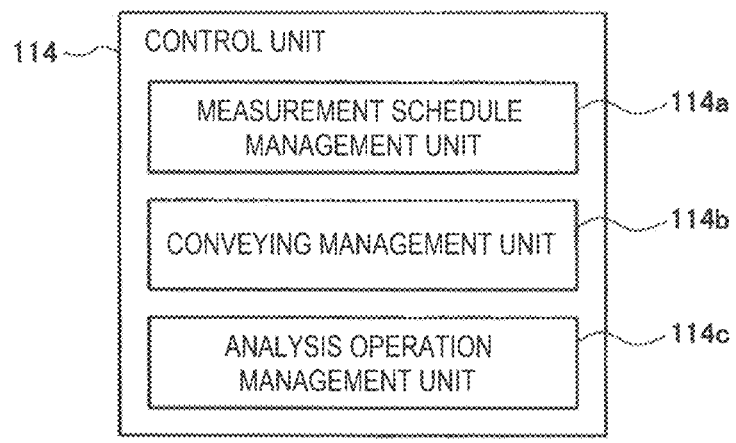

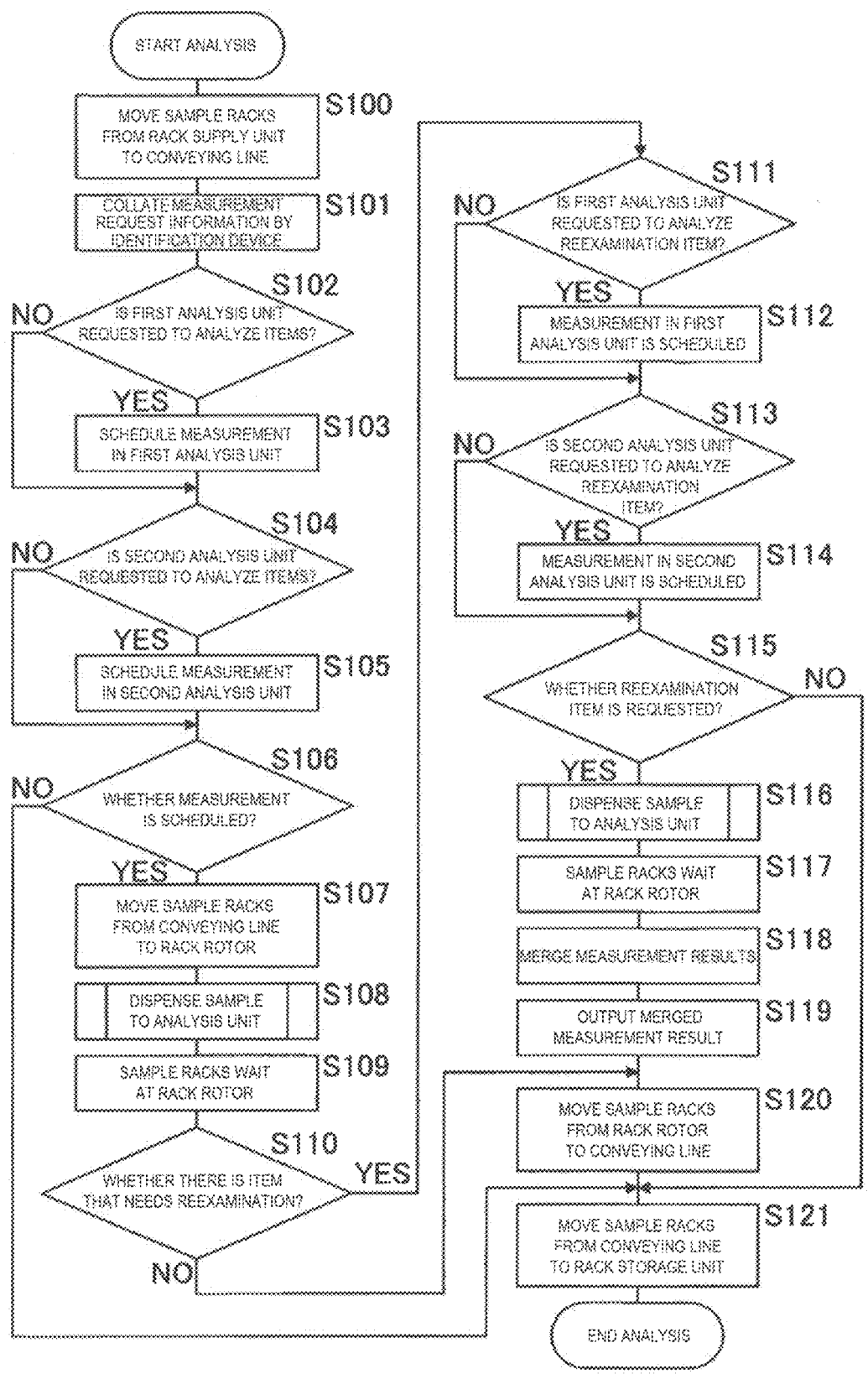
[FIG. 3]

[FIG. 4]
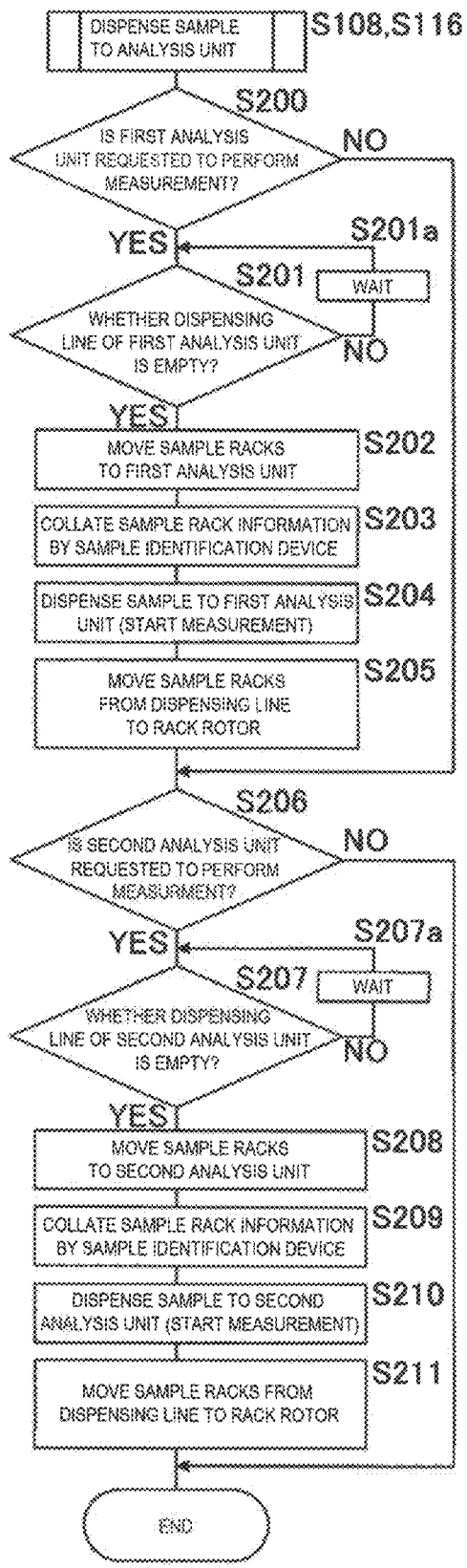

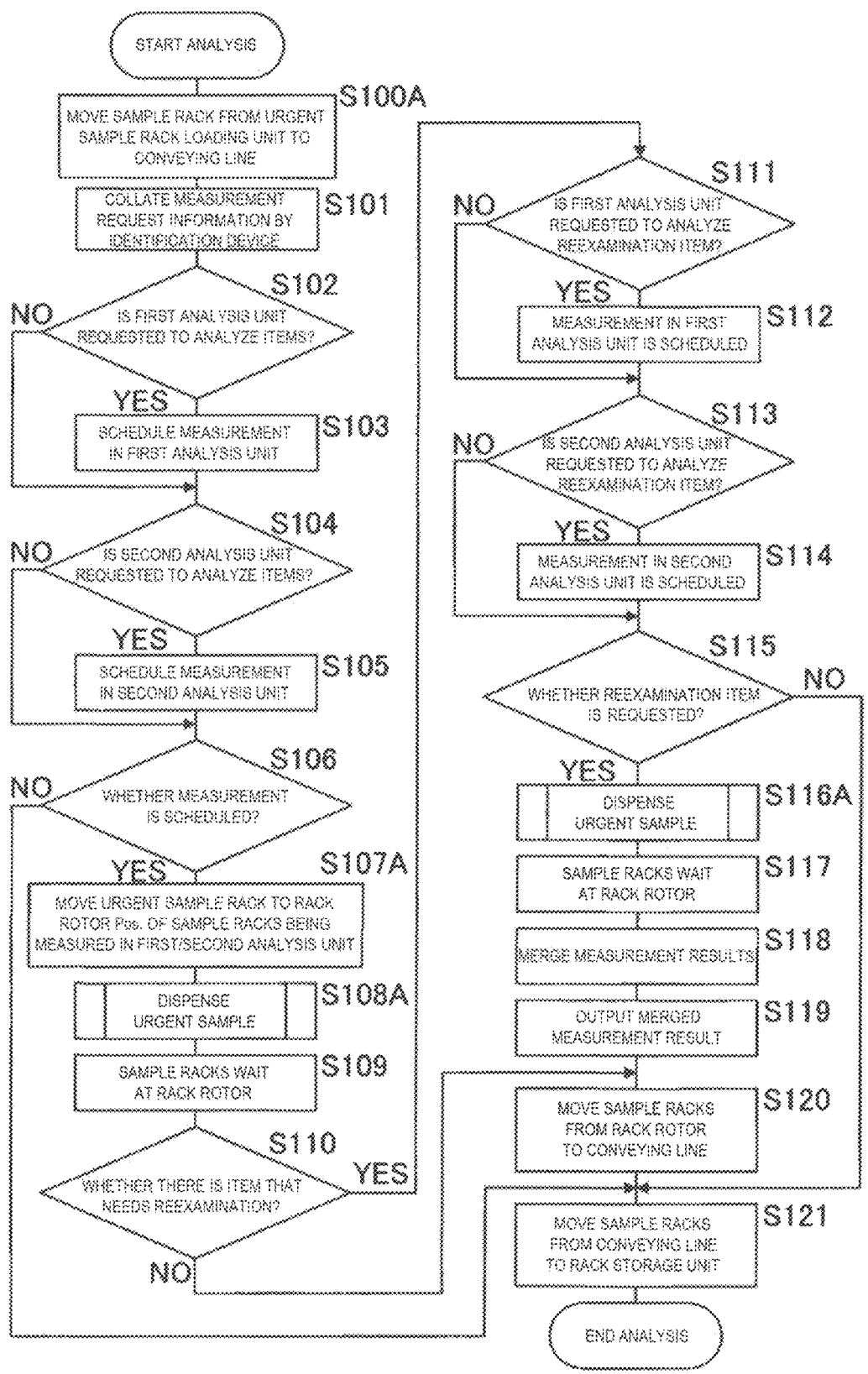
[FIG. 5]

[FIG. 6]
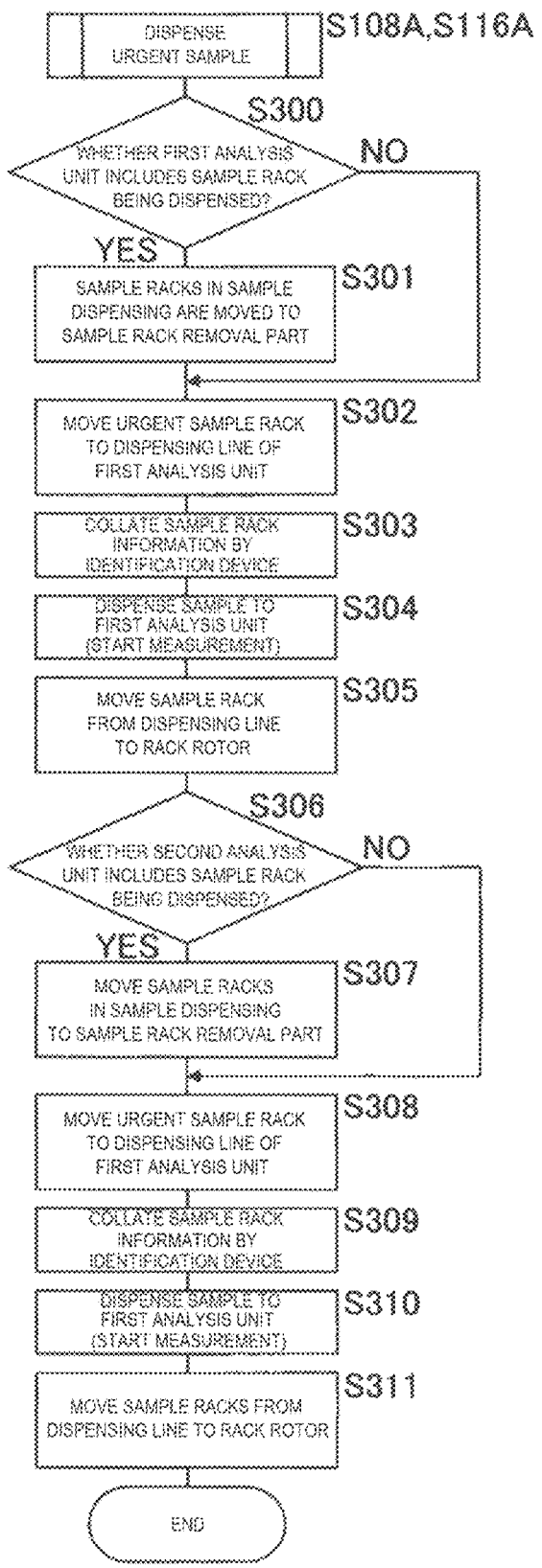

[FIG. 7]
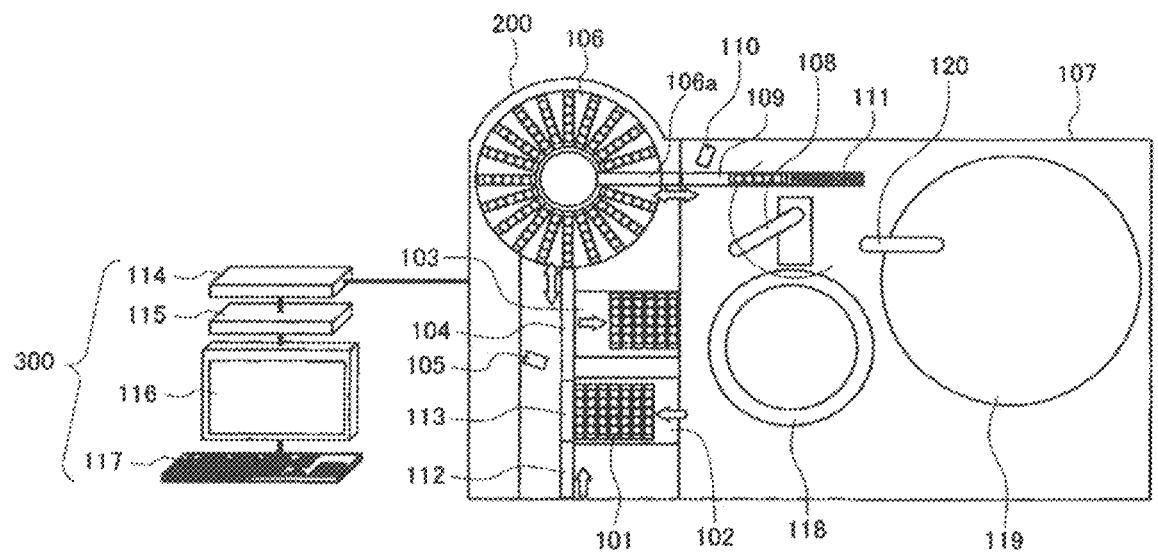
[FIG. 8A]
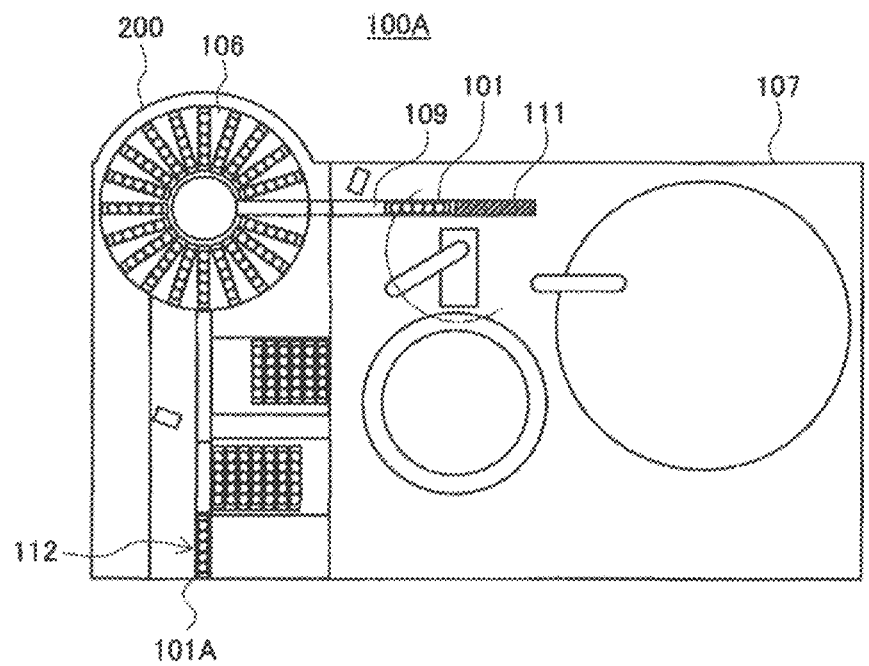

[FIG. 8B]
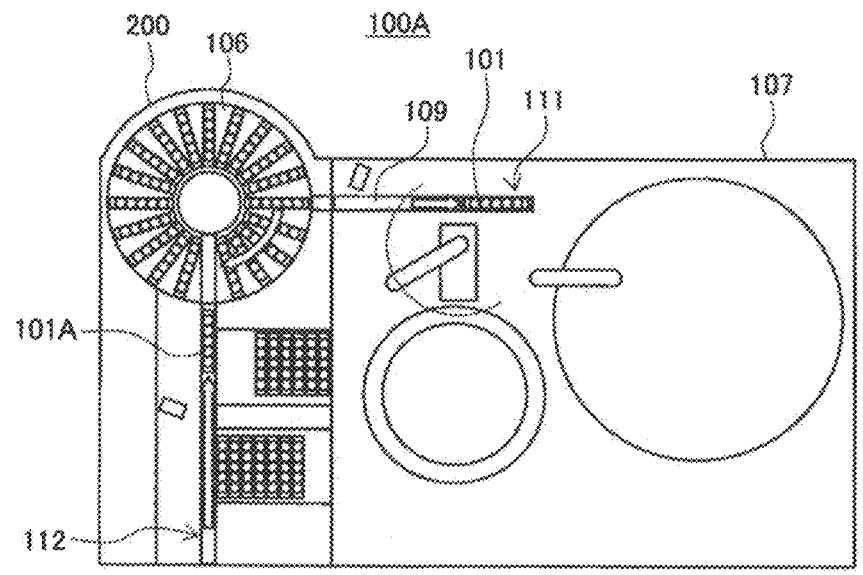
[FIG. 8C]
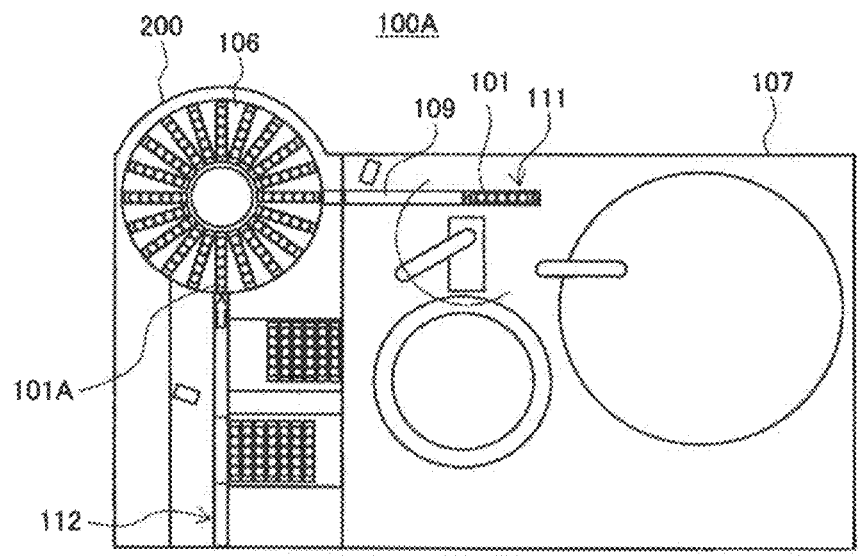

[FIG. 8D]
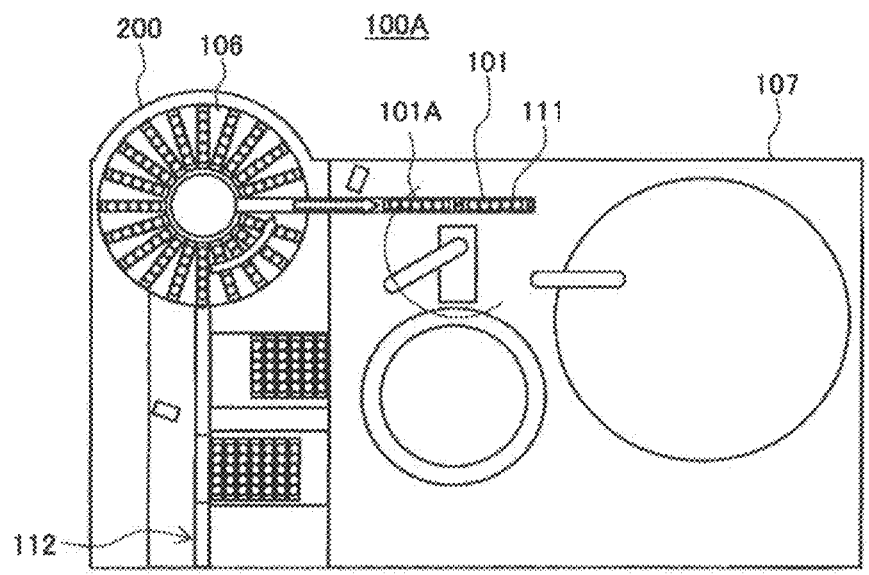
[FIG. 9A]
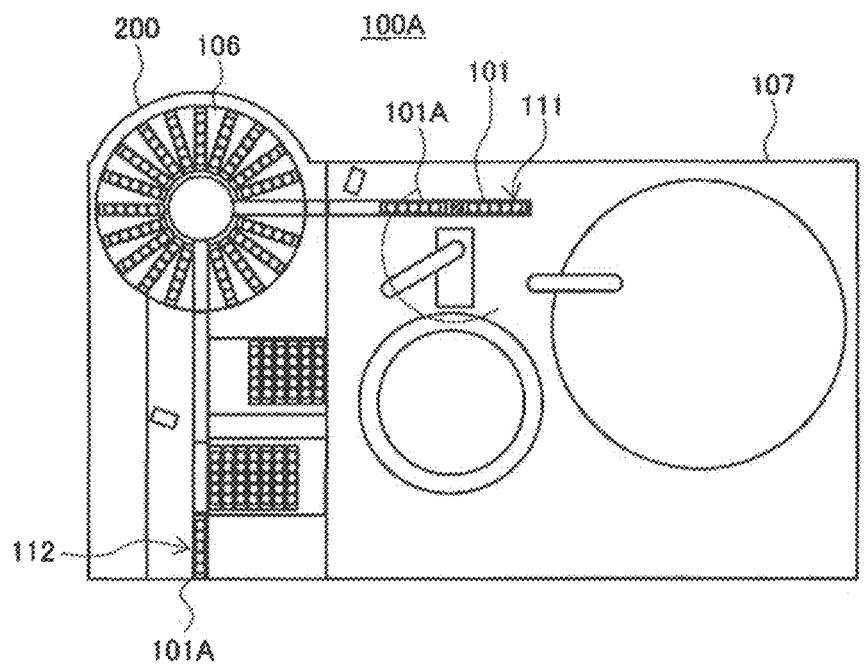

[FIG. 9B]
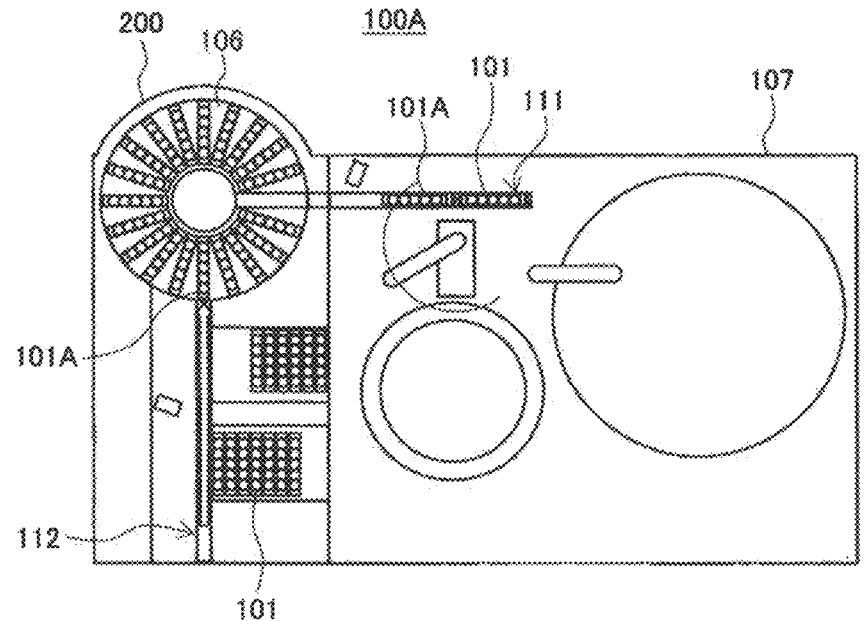
[FIG. 10A]
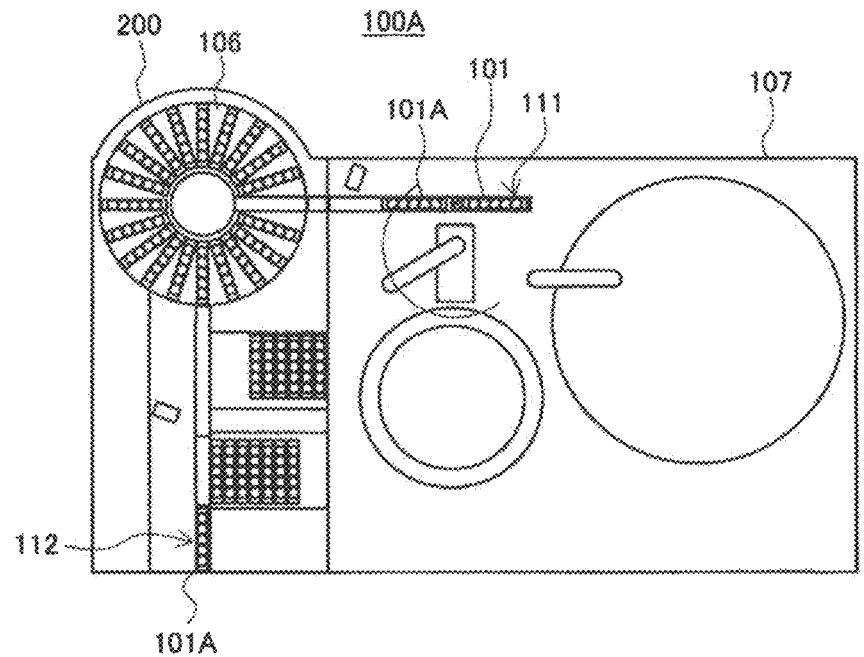

[FIG. 10B]
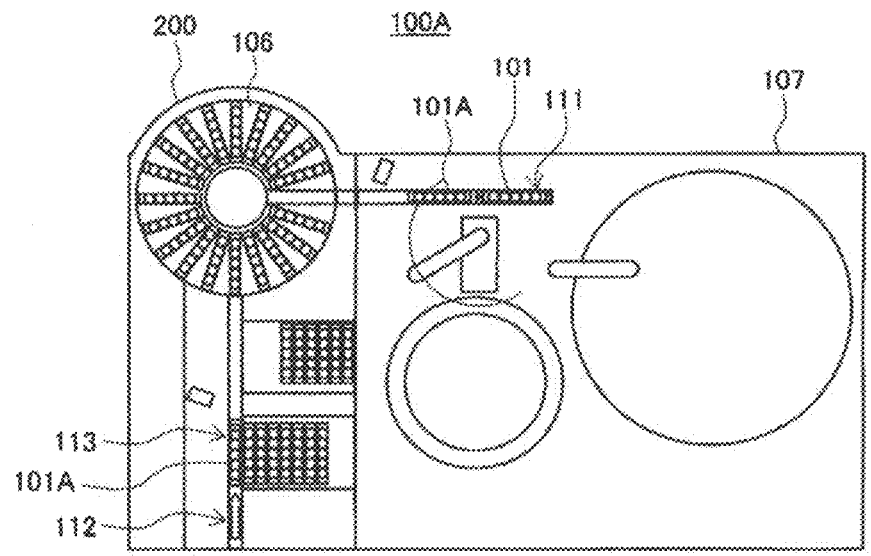
[FIG. 10C]
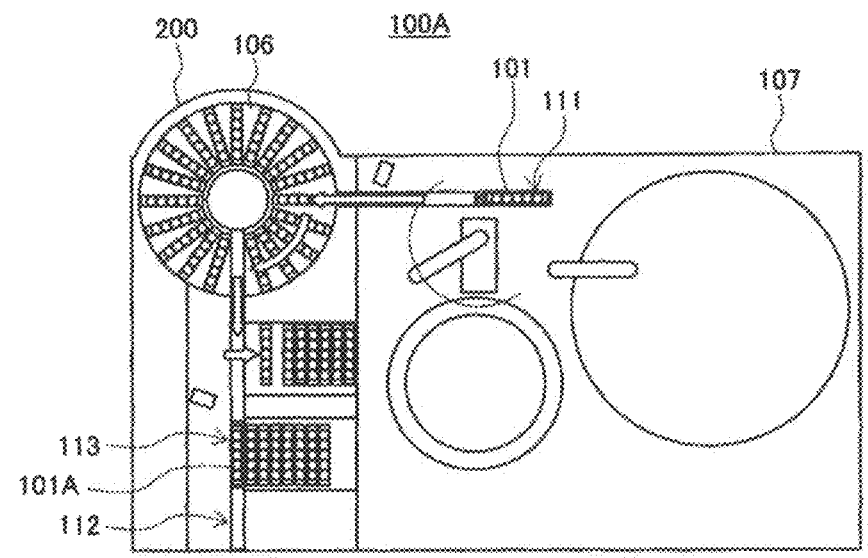

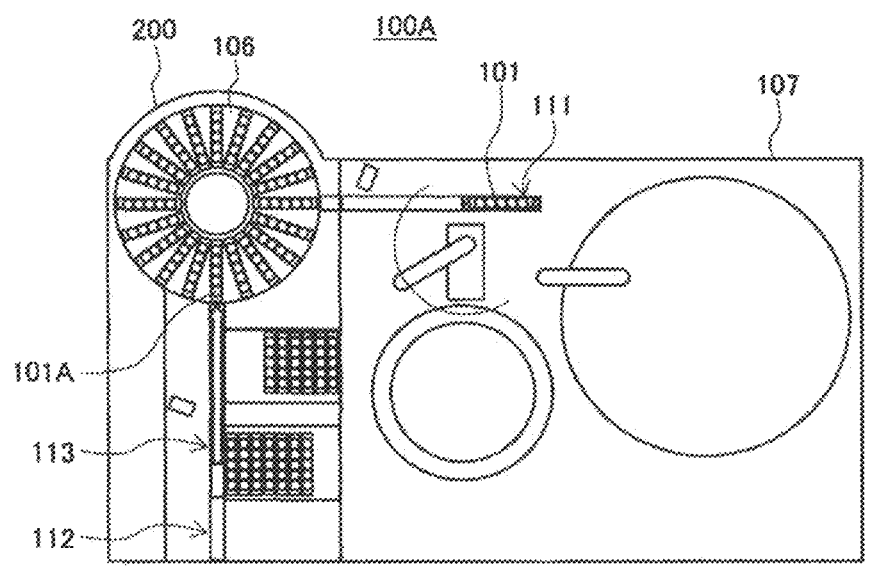
[FIG. 10D]

AUTOMATED ANALYZER

TECHNICAL FIELD

The present invention relates to an automated analyzer for performing qualitative and quantitative analysis of biological samples such as blood and urine.

BACKGROUND ART

In an automated analyzer used for a clinical examination, qualitative and quantitative analysis of specified analysis items is automatically performed on biological samples (hereinafter referred to as specimens or samples) such as blood, plasma, serum, urine, and other body fluids. As such an automated analyzer, there has been known a stand-alone type one in which an analysis unit for analyzing a sample is operated as an independent device, or a module type one in which a plurality of analysis units in different types of analysis fields such as biochemistry and immunity are connected by a sample rack conveying line and operated as a single device.

In a configuration in which the sample rack is conveyed by the conveying line to each analysis unit as in the automated analyzer of the module type, there is a problem in handling a case where an urgent sample requiring urgent analysis is preferentially conveyed to the analysis unit. Regarding such a problem, Patent Literature 1 (JP-A-2016-048255) discloses an automated analyzer including a conveying line configured to convey a sample rack which houses a specimen container for holding a specimen; a plurality of analysis units arranged along the conveying line, configured to have a dispensing line in which a plurality of the sample racks waiting for sample dispensing are capable of waiting, and configured to analyze and measure components included in the specimen; a sampling area configured to dispense the sample to the analysis unit; an identification device provided in the conveying line on an upstream side of the analysis unit and configured to read analysis request information on the specimen; and a control unit configured to determine a conveyance path of the sample rack from the analysis request information read by the identification device, in which a rack removal area is provided in the dispensing line and at a position adjacent to the upstream side of the sampling area, and when the sample rack is present in the sampling area at the time of measuring the urgent specimen, the control unit moves the sample rack to the removal area and positions an urgent sample rack from a downstream side of the sampling area to the sampling area.

PRIOR ART LITERATURE

Patent Literature

PTL 1: JP-A-2016-048255

SUMMARY OF INVENTION

Technical Problem

As in the related art, in addition to the conveying line for conveying the sample rack from a rack supply unit to the analysis unit and a return line arranged along the conveying line and configured to return the sample rack to a rack storage unit and the like, in an environment in which a relatively large automated analyzer is used in which each analysis unit has the dispensing line which is along the conveying line and which makes the plurality of the sample racks waiting for sample dispensing capable of waiting, the degree of freedom in the number and arrangement of each configuration in the automated analyzer and the movement of the sample rack between the lines is very high. Therefore, by applying the related art in which the sample rack being sampled in the sampling area of the dispensing line is moved to the upstream side and the urgent rack conveyed by the conveying line from the downstream side of the dispensing line is positioned to the sampling area, it is possible to easily convey the urgent sample using conveying resource and conveying time relatively freely.

Meanwhile, in a relatively small automated analyzer, the conveying resource is limited as compared with the large automated analyzer and emphasis is placed on speed. Therefore, it is difficult to convey the urgent sample while maintaining the speed required for the relatively small automated analyzer.

The invention has been made in view of the above, and an object of the invention is to provide an automated analyzer capable of conveying an urgent sample while suppressing device complexity, preventing cost from increasing, and also maintaining the speed.

Solution to Problem

In order to achieve the above object, the invention includes one or more dispensing lines that are configured to load and unload, at one end thereof, a sample rack mounted with one or more sample containers housing a sample for analysis and to convey the sample rack back and forth to a dispensing position for dispensing the sample from the sample containers; and a sample rack removal part that is provided adjacent to the other end side of the dispensing lines and provides and receives the sample rack to and from the dispensing lines.

Advantageous Effect

It is possible to convey an urgent sample while suppressing device complexity, preventing cost from increasing, and also maintaining the speed.

BRIEF DESCRIPTION OF DRAWINGS

FIG. 1 is a view schematically showing an overall configuration of an automated analyzer according to an embodiment of the invention.

FIG. 2 is a functional block diagram showing processing content of a control unit in the automated analyzer.

FIG. 3 is a flowchart showing processing content of sample conveying processing when a sample rack is loaded.

FIG. 4 is a flowchart showing processing content of sample dispensing processing in the sample conveying processing when the sample rack is loaded.

FIG. 5 is a flowchart showing processing content of the sample conveying processing when an urgent sample rack is loaded.

FIG. 6 is a flowchart showing processing content of the sample dispensing processing in the sample conveying processing when the urgent sample rack is loaded.

FIG. 7 is a diagram schematically showing an overall configuration of another example of the automated analyzer to which the invention is applied.

FIG. 8A is a diagram illustrating sample conveying processing in a case where an urgent sample rack is loaded into an urgent sample rack loading unit.

FIG. 8B is a diagram illustrating the sample conveying processing in the case where the urgent sample rack is loaded into the urgent sample rack loading unit.

FIG. 8C is a diagram illustrating the sample conveying processing in the case where the urgent sample rack is loaded into the urgent sample rack loading unit.

FIG. 8D is a diagram illustrating the sample conveying processing in the case where the urgent sample rack is loaded into the urgent sample rack loading unit.

FIG. 9A is a diagram illustrating the sample conveying processing in a case where another urgent sample rack is loaded into the urgent sample rack loading unit during the dispensing processing of the urgent sample rack and two or more empty slots of a rack rotor are present.

FIG. 9B is a diagram illustrating the sample conveying processing in the case where the other urgent sample rack is loaded into the urgent sample rack loading unit during the dispensing processing of the urgent sample rack and two or more empty slots of the rack rotor are present.

FIG. 10A is a diagram illustrating the sample conveying processing in a case where the other urgent sample rack is loaded into the urgent sample rack loading unit during the dispensing processing of the urgent sample rack and only one empty slot of the rack rotor is present.

FIG. 10B is a diagram illustrating the sample conveying processing in the case where the other urgent sample rack is loaded into the urgent sample rack loading unit during the dispensing processing of the urgent sample rack and only one empty slot of the rack rotor is present.

FIG. 10C is a diagram illustrating the sample conveying processing in a case where the other urgent sample rack is loaded into the urgent sample rack loading unit during the dispensing processing of the urgent sample rack and only one empty slot of the rack rotor is present.

FIG. 10D is a diagram illustrating the sample conveying processing in the case where the other urgent sample rack is loaded into the urgent sample rack loading unit during the dispensing processing of the urgent sample rack and only one empty slot of the rack rotor is present.

DESCRIPTION OF EMBODIMENTS

An embodiment of the invention will be described below with reference to the drawings.

FIG. 1 is a diagram schematically showing an overall configuration of an automated analyzer according to the present embodiment. Further, FIG. 2 is a functional block diagram showing processing content of a control unit in the automated analyzer.

In FIG. 1, a module type automated analyzer 100 shown as an example in the present embodiment includes a plurality of (two in the present embodiment) analysis modules (analysis unit) 107, 207, a sample rack conveying module 200 for conveying sample racks 101 mounted with one or more sample containers housing a sample to be analyzed in the analysis modules 107, 207, and a control device 300 for controlling overall operation of the automated analyzer 100.

In the sample racks 101 handled by the automated analyzer 100, one or more sample containers housing a biological sample (hereinafter referred to as "a specimen or a sample") such as blood, plasma, serum, urine, and other body fluids to be subjected to qualitative and quantitative analysis in the automated analyzer 100 are mounted. The sample racks 101 include at least a sample rack (hereinafter, simply referred to as the sample rack 101) mounted with sample containers housing a sample (normal sample) to be analyzed in a normal priority, and a sample rack (hereinafter referred to as an urgent sample rack 101A when particularly distinguished from the sample racks 101) mounted with a sample container housing an urgent sample that has a higher degree of urgency for analysis measurement than the sample rack.

The analysis modules 107, 207 perform sampling (dispensing) on the sample housed in the sample containers mounted on the sample racks 101 and perform qualitative and quantitative analysis. The analysis modules 107, 207 include dispensing lines 109, 209 of, for example, belt conveyor type, that each loads the sample rack 101 conveyed by the sample rack conveying module 200 from one end thereof and conveys the sample rack back and forth to a dispensing position for dispensing the sample from the sample containers; a sample rack removal part 111, 112 that is provided adjacent to the other ends of the dispensing lines 109, 209 and provides and receives the sample rack to and from the dispensing lines 109, 209; sample identification devices 110, 210 that read and identify an identification medium (not shown) such as an RFID or a bar code provided on the sample racks 101 and the sample containers in order to collate analysis request information for the sample housed in the sample racks 101 loaded into the dispensing lines 109, 209; sample dispensing mechanisms 108, 208 that dispense the sample from the sample containers of the sample racks 101 conveyed to the dispensing positions on the dispensing lines 109, 209 to reaction containers of reaction disks 118, 218; reagent dispensing mechanisms 120, 220 that dispense reagent contained in reagent containers of reagent disks 119, 219 into reaction containers of the reaction disks 118, 218; and measuring units (not shown) that measure mixed liquid (reaction liquid) of the sample and the reagent dispensed into the reaction containers and perform qualitative and quantitative analysis, respectively.

The dispensing lines 109, 209 adopt a conveying mechanism capable of repeating an operation in which the sample racks 101 are drawn from the sample rack conveying module 200 to the analysis modules 107, 207 and passed from the analysis modules 107, 207 to the sample rack conveying module 200. Although belt conveyor type conveying mechanisms are adopted as the dispensing lines 109, 209 in the present embodiment, a configuration may be adopted in which conveying is realized by fitting projection parts driven along the dispensing lines 109, 209 into recess parts provided in the sample racks 101 in advance.

It is sufficient that the sample rack removal parts 111, 211 can provide and receive the sample racks 101 to and from the other ends (end on the side different from the end on the side of sample rack conveying module 200) of the dispensing lines 109, 209, but in the present embodiment, for example, the sample rack removal lines 111, 211, such as belt conveyor type ones, are provided so as to continuously convey the sample racks 101 back and forth between the sample rack removal lines 111, 211 and the other ends of the dispensing lines 109, 209. A configuration is also applicable in which the dispensing lines 109, 209 and the sample rack removal lines 111, 211 are configured by a single belt conveyor, and a stopper is provided to limit movement of the sample racks 101 from a range that configures the sample rack removal lines 111, 211 to a range that configures the dispensing lines 109, 209 and movement of the sample racks 101 from the range that configures the dispensing lines 109, 209 to the sample rack conveying module 200.

The analysis modules installed in the automated analyzer 100 need not be the same type, and biochemical analysis modules, immunoanalysis modules, blood coagulation analysis modules, and the like can be appropriately arranged according to specification environment.

The sample rack conveying module 200 conveys the sample racks 101 loaded into the automated analyzer 100 to and from the analysis modules 107, 207, and includes a conveying line 104, for example, a belt conveyor type one, that conveys the sample rack back and forth; an urgent sample rack loading unit 112 provided adjacent to the conveying line 104 and for loading the urgent sample rack 101A; a sample rack supply unit 102 provided adjacent to the transfer line 104 and closer to one end of the conveying line 104 than the urgent sample rack loading unit 112 and for supplying the sample racks 101 of the normal sample; a sample rack storage unit 103 provided adjacent to the conveying line 104 and closer to the one end of the conveying line 104 than the sample rack supply unit 102 and for storing the sample racks 101; an urgent sample rack wait area 113 provided on the conveying line 104 and closer to the other end of the conveying line 104 than the sample rack storage unit 103 and for causing the urgent sample rack 101A to temporarily wait therein; a rack rotor 106 provided on one end of the conveying line 104, having one or more slots (for example, slots of empty positions 106a, 106b: empty slots) in which the sample racks 101 can be mounted, and providing and receiving the sample rack between one end of the conveying line 104 and one end of one or more dispensing lines; and a sample identification device 105 that reads and identifies an identification medium (not shown) such as an RFID or a bar code provided on the sample racks 101 and the sample containers in order to collate analysis request information for the sample housed in the sample containers mounted on the sample racks 101 conveyed by the conveying line 104.

The control device 300 controls the overall operation of the automated analyzer 100 and includes a display unit 116 that displays an input screen of various parameters and settings, analysis inspection data of initial examination or reexamination, measurement results, and the like; an input unit 117 for inputting various parameters and settings, analysis request information, instructions for starting analysis, and the like, a storage unit 115 that stores various parameters, settings, measurement results, analysis request information of the sample housed in the sample containers mounted on each sample rack, and the like; and a control unit 114 that controls the overall operation of the automated analyzer 100 including the control device 300.

In FIG. 2, the control unit 114 includes a measurement schedule management unit 114a that manages a measurement schedule of the sample racks 101 loaded into the automatic analyzer 100, a conveying management unit 114b that manages conveyance of the sample racks 101 in the automatic analyzer 100, and an analysis operation management unit 114c that manages a series of analysis operations including dispensing processing in the analysis units 107, 207. In FIG. 2, only functional blocks related to sample conveying processing are extracted from the processing content of the control unit 114 and shown.

FIG. 3 is a flowchart showing the processing content of the sample conveying processing when the sample rack (normal sample) is loaded. FIG. 4 is a flowchart showing the processing content of the sample dispensing processing in the sample conveying processing when the sample rack (normal sample) is loaded. FIG. 5 is a flowchart showing the processing content of the sample conveying processing when the urgent sample rack is loaded. FIG. 6 is a flowchart showing the processing content of the sample dispensing processing in the sample conveying processing when the urgent sample rack is loaded. Here, the two analysis units 107, 207 are described as a first analysis unit 107 and a second analysis unit 207, respectively.

In FIG. 3, when an analysis is requested by the input unit 117, the control unit 114 starts various operations related to the analysis. First, one of the sample racks 101 of the normal sample arranged parallel to the sample rack supply unit 102 is moved to the conveying line 104 (step S100), and then the sample rack numbers and the sample container numbers are recognized by reading the identification medium attached to the sample racks 101 and the sample containers by the sample identification device 105, and the analysis request information is inquired using the numbers (step S101). The inquiry of the analysis request information is performed by transmitting the sample rack numbers and the sample container numbers recognized by the sample identification device 105 to the control unit 114, collating the type of the sample racks 101 and the type of analysis items specified for the sample containers with the matched information which has been corresponded to a specimen reception number and has been designated by the input unit 117 in advance. The destination of the sample racks 101 is determined by the control unit 114 on the basis of the collation result, stored in the storage unit 115 and then used in the conveying processing of the sample rack 101.

Subsequently, it is determined whether the samples of the sample racks 101 are requested to be analyzed by the first analysis unit 107 (step S102), and if the determination result is YES, measurement in the first analysis unit 107 is scheduled (step S103). If the determination result in step S102 is NO or when the processing of step S103 is completed, it is subsequently determined whether the sample of the sample racks 101 is requested to be analyzed by the second analysis unit 207 (step S104), and if the determination result is YES, measurement in the second analysis unit 207 is scheduled (step S105). If the determination result instep S104 is NO, or when the processing of step S105 is completed, it is determined whether measurement is scheduled in at least one of the first analysis unit 107 and the second analysis unit 207. If the determination result is NO, the sample racks 101 are moved from the conveying line 104 to the sample rack storage unit 103 (step S121), and the sample conveying processing is ended.

If the determination result in step S106 is YES, the sample racks 101 are moved from the conveying line 104 to the rack rotor 106 (step S107), and the sample dispensing processing is performed in the analysis units 107, 207 where the measurement is scheduled (step S108).

In FIG. 4, the control unit 114 determines whether the first analysis unit 107 is requested to perform measurement (step S200), and if the determination result is YES, it is determined whether the dispensing line 109 is empty, that is, whether there are no sample racks 101 being analyzed in the dispensing line 109 (step S201). If the determination result in step S201 is NO, the rack rotor 106 waits until the determination result in step S201 is YES (step S201a). If the determination result in step S201 is YES, the rack rotor 106 rotates and the sample racks 101 are positioned at one end of the dispensing line 109 and are drawn into the first analysis unit 107, whereby the sample racks 101 are moved to the first analysis unit 107 (step S202). Subsequently, the sample identification device 110 collates the analysis request information of the sample racks 101 moved into the dispensing line 109 (step S203), and the sample is dispensed to the reaction container by inserting a dispensing probe of the sample dispensing mechanism 108 into the sample container, and the measurement is started (step S204). When two or more inspection items are specified for the same sample container and when an examination item is specified for another sample container on the same sample rack 101, the dispensing operation of the sample is subsequently repeated. The sample racks 101, in which the sample regarding all the specified analysis items has been dispensed to the first analysis unit 107, are moved from the dispensing line 109 to the rack rotor 106 (step S205).

Subsequently, it is determined whether the second analysis unit 207 is requested to perform measurement (step S206), and if the determination result is YES, it is determined whether the dispensing line 209 is empty, that is, whether there are sample racks 101 being analyzed in the dispensing line 209 (step S207). If the determination result in step S207 is NO, the rack rotor 106 waits until the determination result instep S207 is YES (step S207a). If the determination result in step S207 is YES, the rack rotor 106 rotates and the sample racks 101 are positioned at one end of the dispensing line 209 and are drawn into the second analysis unit 207, whereby the sample racks 101 are moved to the second analysis unit 207 (step S208). Subsequently, the sample identification device 210 collates the analysis request information of the sample racks 101 moved into the dispensing line 209 (step S209), and the sample is dispensed to the reaction container by inserting a dispensing probe of the sample dispensing mechanism 208 is into the sample container specified to be analyzed, and the measurement is started (step S210). When two or more inspection items are specified for the same sample container and when an examination item is specified for another sample container on the same sample rack 101, the dispensing operation of the sample is subsequently repeated. The sample racks 101, in which the sample regarding all the specified analysis items has been dispensed to the second analysis unit 207, are moved from the dispensing line 109 to the rack rotor 106 (step S211).

Return to FIG. 3.

The sample racks 101 of which the sample dispensing processing in the analysis units 107, 207 is completed wait at the rack rotor 106 (step S109), and are determined whether there is an item that needs reexamination (step S110). Since the sample rack numbers of the sample racks 101 moved to the rack rotor 106 are stored in the storage unit 115, at this time, the control unit 114 has already determined the sample rack 101 that does not require reexamination, such as a control sample rack, a standard sample rack, and a cleaning solution rack or the sample rack 101 that may need reexamination. That is, the sample collected in the reaction containers on the reaction disks 118, 218 of the analysis units 107, 207 is reacted with the reagent dispensed by the reagent dispensing mechanisms 120, 220. Data corresponding to each analysis item measured after a prescribed time is output to the control unit 114. The control unit 114 collates preset determination criteria with the analysis examination data, and if the measurement data is incorrect, associates the sample that needs reexamination with the sample rack number and the sample container number, and stores the number in the storage unit 115. Therefore, if the determination result in step S110 is NO, the sample racks 101 are moved from the rack rotor 106 to the sample rack storage unit 103 via the conveying line 104 (step S120, step S121), and the sample conveying processing is ended. If the determination result in step S110 is YES, it is determined whether a reexamination item by the first analysis unit 107 is requested for the sample in the sample racks 101 (step S111), and if the determination result is YES, the measurement in the first analysis unit 107 is scheduled (step S112).

If the determination result in step S111 is NO or when the processing of step S112 is completed, it is subsequently determined whether a reexamination item by the second analysis unit 107 is requested for the sample in the sample racks 101 (step S113), and if the determination result is YES, the measurement in the second analysis unit 207 is scheduled (step S114). In addition, if the determination result in step S113 is NO, or when the processing of step S114 is completed, it is subsequently determined whether the measurement of the reexamination item is scheduled in at least one of the first analysis unit 107 and the second analysis unit 207 (step S115), and if the determination result is NO, the sample racks 101 are moved from the conveying line 104 to the sample rack storage unit 103 (step S121), and the sample conveying processing is ended.

If the determination result in step S115 is YES, the sample dispensing processing is performed in the analysis units 107, 207 in which the measurement of the reexamination item is scheduled (step S116). The processing of step S116 is the same as the processing of step S108. The sample racks 101 of which the sample dispensing processing in the analysis units 107, 207 is completed wait at the rack rotor 106 (step S117). The measurement results of the first analysis examination data and the analysis examination data of the reexamination are merged (step S118), and the merged measurement result is output (displayed) to the display unit 116 (step S119). Thereafter, the sample racks 101 are moved from the rack rotor 106 to the sample rack storage unit 103 via the conveying line 104 (step S120, step S121), and the sample conveying processing is ended.

Next, sample conveying processing when the urgent sample rack 101A is loaded into the urgent sample rack loading unit 112 will be described.

In FIG. 5, when an urgent sample analysis is requested by the input unit 117, the control unit 114 starts various operations related to the analysis. First, when the urgent sample rack 101A is loaded into the urgent sample rack loading unit 112, the urgent sample rack 101A is moved from the urgent sample rack loading unit 112 to the conveying line 104 (step S100A), and then the sample rack numbers and the sample container numbers are recognized by reading the identification medium attached to the urgent sample rack 101A and the sample containers by the sample identification device 105, and the analysis request information is inquired using the numbers (step S101). The inquiry of the analysis request information is performed by transmitting the sample rack numbers and the sample container numbers recognized by the sample identification device 105 to the control unit 114, collating the type of the urgent sample rack 101A and the type of analysis items specified for the sample containers with sample reception number with the matched information which has been corresponded to a specimen reception number and has been designated by the input unit 117 in advance. The destination of the urgent sample rack 101A is determined by the control unit 114 on the basis of the collation result, stored in the storage unit 115 and then used in the conveying processing of the urgent sample rack 101A.

Subsequently, it is determined whether the sample of the urgent sample rack 101A is requested to be analyzed by the first analysis unit 107 (step S102), and if the determination result is YES, measurement in the first analysis unit 107 is scheduled (step S103). If the determination result in step S102 is NO or when the processing of step S103 is completed, it is subsequently determined whether the sample of the urgent sample rack 101A is requested to be analyzed by the second analysis unit 207 (step S104), and if the determination result is YES, measurement in the second analysis unit 207 is scheduled (step S105). If the determination result in step S104 is NO, or when the processing of step S105 is completed, it is determined whether measurement is scheduled in at least one of the first analysis unit 107 and the second analysis unit 207. If the determination result is NO, the urgent sample rack 101A is moved from the conveying line 104 to the sample rack storage unit 103 (step S121), and the sample conveying processing is ended.

If the determination result in step S106 is YES, empty positions 106a, 106b for the sample racks 101 being analyzed by the first analysis unit 107 and the second analysis unit 207 (hereinafter, empty positions in analysis) are positioned on the conveying line 104, the urgent sample rack 101A is moved to the empty positions 106a, 106b in analysis (step S107A), and the sample dispensing processing is performed in the analysis units 107, 207 in which the measurement is scheduled (step S108A).

In FIG. 6, the control unit 114 determines whether the dispensing line 109 is empty, that is, whether the dispensing line 109 includes the sample rack 101 being dispensed (step S300). If the determination result in step S300 is YES, the sample racks 101 in sample dispensing are moved to the sample rack removal part 111 (step S301). If the determination result in step S300 is NO or when the processing of step S301 is completed, the rack rotor 106 rotates and the urgent sample rack 101A is positioned at one end of the dispensing line 109 and is drawn into the first analysis unit 107, whereby the urgent sample rack 101A is moved to the first analysis unit 107 (step S302). Subsequently, the sample identification device 110 collates the analysis request information of the urgent sample rack 101A moved into the dispensing line 109 (step S303), and the sample is dispensed to the reaction container by inserting a dispensing probe of the sample dispensing mechanism 108 into the sample container specified to be analyzed, and the measurement is started (step S204). When two or more examination items are specified for the same sample container and when an examination item is specified for another sample container on the same urgent sample rack 101A, the dispensing operation of the sample is subsequently repeated. The urgent sample rack 101A, in which the sample regarding all the specified analysis items has been dispensed to the first analysis unit 107, is moved from the dispensing line 109 to the rack rotor 106 (step S305).

Subsequently, it is determined whether or not the dispensing line 209 is empty, that is, whether the dispensing line 209 includes the sample racks 101 being dispensed (step S306). If the determination result in step S306 is YES, the sample racks 101 in sample dispensing are moved to the sample rack removal part 211 (step S307). If the determination result in step S306 is NO or when the processing of step S307 is completed, the rack rotor 106 rotates and the urgent sample rack 101A is positioned at one end of the dispensing line 209 and is drawn into the second analysis unit 207, whereby the urgent sample rack 101A is moved to the second analysis unit 207 (step S308). Subsequently, the sample identification device 210 collates the analysis request information of the urgent sample rack 101A moved into the dispensing line 209 (step S309), and the sample is dispensed to the reaction container by inserting a dispensing probe of the sample dispensing mechanism 208 is into the sample container specified to be analyzed, and the measurement is started (step S210). When two or more examination items are specified for the same sample container and when an examination item is specified for another sample container on the same urgent sample rack 101A, the dispensing operation of the sample is subsequently repeated. The urgent sample rack 101A, in which the sample regarding all the specified analysis items has been dispensed to the second analysis unit 207, is moved from the dispensing line 209 to the rack rotor 106 (step S311).

Return to FIG. 5.

The urgent sample rack 101A of which the sample dispensing processing in the analysis units 107, 207 is completed waits at the rack rotor 106 (step S109), and are determined whether there is an item that needs reexamination (step S110). Since the sample rack number of the urgent sample rack 101A moved to the rack rotor 106 is stored in the storage unit 115, at this time, the control unit 114 has already determined the sample rack 101 that does not require reexamination, such as a control sample rack, a standard sample rack, and a cleaning solution rack or the urgent sample rack 101A that may need reexamination. That is, the sample collected in the reaction containers on the reaction disks 118, 218 of the analysis units 107, 207 is reacted with the reagent dispensed by the reagent dispensing mechanisms 120, 220. Data corresponding to each analysis item measured after a prescribed time is output to the control unit 114. The control unit 114 collates preset determination criteria with the analysis examination data, and if the measurement data is incorrect, associates the sample that needs reexamination with the sample rack number and the sample container number, and stores the number in the storage unit 115. Therefore, if the determination result in step S110 is NO, the urgent sample rack 101A is moved from the rack rotor 106 to the sample rack storage unit 103 via the conveying line 104 (step S120, step S121), and the sample conveying processing is ended. If the determination result in step S110 is YES, it is determined whether a reexamination item by the first analysis unit 107 is requested for the sample in the urgent sample rack 101A (step S111), and if the determination result is YES, the measurement in the first analysis unit 107 is scheduled (step S112). If the determination result in step S111 is NO or when the processing of step S112 is completed, it is subsequently determined whether a reexamination item by the second analysis unit 107 is requested for the sample in the urgent sample rack 101A (step S113), and if the determination result is YES, the measurement in the second analysis unit 207 is scheduled (step S114). In addition, if the determination result in step S113 is NO, or when the processing of step S114 is completed, it is subsequently determined whether the measurement of the reexamination item is scheduled in at least one of the first analysis unit 107 and the second analysis unit 207 (step S115), and if the determination result is NO, the urgent sample rack 101A is moved from the conveying line 104 to the sample rack storage unit 103 (step S121), and the sample conveying processing is ended.

If the determination result in step S115 is YES, the sample dispensing processing is performed in the analysis units 107, 207 in which the measurement of the reexamination item is scheduled (step S116A). The processing of step S116A is the same as the processing of step S108A. The urgent sample rack 101A of which the sample dispensing processing in the analysis units 107, 207 is completed waits at the rack rotor 106 (step S117). The measurement results of the first analysis examination data and the analysis examination data of the reexamination are merged (step S118), and the merged measurement result is output (displayed) to the display unit 116 (step S119). Thereafter, the urgent sample rack 101A is moved from the rack rotor 106 to the sample rack storage unit 103 via the conveying line 104 (step S120, step S121), and the sample conveying processing of the urgent sample rack 101A is ended.

The operation of the present embodiment configured as described above will be described with reference to the drawings.

FIG. 7 is a diagram schematically showing an overall configuration of another example of the automated analyzer to which the present invention is applied.

As shown in FIG. 7, the present invention applied to the automated analyzer 100 of the present embodiment can be applied to a case where only one analysis unit 107 is used, and an effect similar to that of the present embodiment can be obtained. Therefore, for simplification of description, the operation and effect of the present embodiment will be described using the automated analyzer 100A shown in FIG. 7 (however, the control device 300 is omitted).

FIGS. 8A to 8D are diagrams illustrating sample conveying processing when an urgent sample rack is loaded into an urgent sample rack loading unit.

When the urgent sample rack 101A is loaded into the urgent sample rack loading unit 112 (FIG. 8A) and when the sample rack 101 is present in the dispensing line 109 of the analyzing unit 107, the sample rack 101 in sample dispensing is moved to the sample rack removal part 111 (FIG. 8B). Further, an empty position during analysis for the sample rack 101 being analyzed in the analysis unit 107 is positioned on the coveying line 104 and the urgent sample rack 101A is moved to the empty position during analysis (FIG. 8C). The rack rotor 106 rotates, the urgent sample rack 101A is positioned at one end of the dispensing line 109 and is drawn into the analysis unit 107, whereby the urgent sample rack 101A is moved to the analysis unit 107 (FIG. 8D). As described above, by utilizing the empty position during the analysis for the urgent sample rack 101A, it is not necessary to secure a slot for the urgent sample rack 101A, and the rack rotor 106 can be efficiently operated.

FIGS. 9A and 9D are diagrams illustrating the sample conveying processing in a case where another urgent sample rack is loaded into the urgent sample rack loading unit during the dispensing processing of the urgent sample rack and two or more empty slots of the rack rotor are present.

In a case where there are two or more empty slots in the rack rotor 106 when the urgent sample rack 101A being sampled is present in the dispensing line 109 (FIG. 9A), the urgent sample rack 101A loaded later is moved to one of two or more empty slots and waits at the rack rotor 106 until the sample dispensing processing of the urgent sample rack 101A in the sample dispensing is completed (FIG. 9B).

FIGS. 10A to 10D are diagrams illustrating sample conveying processing in a case where another urgent sample rack is loaded into the urgent sample rack loading unit during the dispensing processing of the urgent sample rack and only one empty slot of the rack rotor is present.

In a case where there is only one empty slot in the rack rotor 106 when the urgent sample rack 101A being sampled is present in the dispensing line 109 (FIG. 10A), the urgent sample rack 101A loaded later is moved to the urgent sample rack wait area 113 adjacent to the downstream of the urgent sample rack loading unit 112 and located at the upstream of the inlet of the sample rack storage unit 103 and waits (FIG. 10B). When the sampling processing of the urgent sample rack 101A in the sampling processing is completed, the urgent sample rack 101A of the dispensing line 109 is moved to the conveying line 104 via the empty position during the analysis and stored in the sample rack storage unit 103 (FIG. 10C). Thereafter, the urgent sample rack 101A waiting in the urgent sample rack waiting area 113 is moved from the conveying line 104 to the empty position during the analysis (FIG. 10D), and the urgent sample analysis is performed.

The effects of the present embodiment configured as described above will be described.

As in the related art, in addition to the conveying line for conveying the sample rack from a rack supply unit to the analysis unit and a return line arranged along the conveying line and configured to return the sample rack to a rack storage unit and the like, in an environment in which a relatively large automated analyzer is used in which each analysis unit has the dispensing line which is along the conveying line and which makes the plurality of the sample racks waiting for sample dispensing capable of waiting, the degree of freedom in the number and arrangement of each configuration in the automated analyzer and the movement of the sample rack between the lines is very high. Therefore, by applying the related art in which the sample rack being sampled in the sampling area of the dispensing line is moved to the upstream side and the urgent sample rack conveyed by the conveying line from the downstream side of the dispensing line is positioned to the sampling area, it is possible to easily convey the urgent sample using conveying resource and conveying time relatively freely. Meanwhile, in a relatively small automated analyzer, the conveying resource is limited as compared with the large automated analyzer and emphasis is placed on speed. Therefore, it is difficult to convey the urgent sample while maintaining the speed required for the relatively small automated analyzer.

In contrast, the present embodiment is provided with one or more dispensing lines 109, 209 that are each for loading and unloading, at one end thereof, the sample rack 101 mounted with one or more sample containers housing the sample for analysis and for conveying the sample rack back and forth to a dispensing position for dispensing the sample from the sample containers and sample rack removal parts 111 and 211 that are provided adjacent to the other ends of the dispensing lines 109, 209 and provide and receive sample racks to and from the dispensing lines 109, 209. According to this configuration, it is possible to convey an urgent sample while suppressing device complexity, preventing cost from increasing, and also maintaining speed.

The automated analyzer 100 having the two-module configuration shown in FIG. 1 may be configured by analysis units having different measurement sensitivities. For example, the analysis unit 107 may be a biochemical analysis unit, and the analysis unit 207 may be an immunoanalysis unit. In this case, since the sample carryover suppression requirement in the immunoanalysis is stricter than that of the biochemical analysis unit, if the same sample is requested for the items of biochemistry and immunity, prioritized rack handling may be required, such as performing the biochemical measurement after the immune measurement is complete. In particular, when the sample to be reexamined for the immunoanalysis is present in the sample racks 101, the waiting time of the sample racks 101 becomes long, and there arises a problem that the overall processing capacity of the automated analyzer 100 decreases and the analysis end time is extended. Therefore, in the automated analyzer to which the present invention is applied, if the analysis item of the analysis unit 207 has a higher priority than the analysis item of the analysis unit 107 and there is an analysis item of the analysis unit 207 with high priority in a sample rack 101, this sample rack 101 is treated in the same priority level as the urgent sample rack. After the sample rack 101 with the highest priority is conveyed to the analysis unit 207 and the sampling of the sample is completed and after it is determined to wait at the rack rotor 106 to be reexamined, the sample racks 101 are conveyed to the analysis unit 107 in a normal analysis order. In this way, it is possible to suppress a decrease in the processing capacity and an extension in the analysis end time.

The invention is not limited to the embodiments described above and includes various modifications. For example, the above-described embodiments are detailed for easy understanding of the invention, but the invention is not necessarily limited to include all the above configurations. In regard to the above-mentioned configurations, functions, and the like, a part thereof or an entirety thereof may be achieved by being designed as an integrated circuit. The above configurations, functions, and the like may be realized by software in such a way that a processor interprets and executes a program for realizing each function.

REFERENCE SIGN LIST

100, 100A . . . automated analyzer, 101 . . . sample rack, 101A . . . urgent sample rack, 102 . . . sample rack supply unit, 103 . . . sample rack storage unit, 104 . . . conveying line, 105 . . . sample identification device, 106 . . . rack rotor, 106a, 106b . . . empty position (empty slot), 107, 207 . . . analysis module (analysis unit), 108, 208 . . . sample dispensing mechanism, 109, 209 . . . dispensing line, 110, 210 . . . sample identification device, 111, 211 . . . sample rack removal part (sample rack removal line), 112 . . . urgent sample rack loading unit, 113 . . . urgent sample rack wait area, 114 . . . control unit, 114a . . . measurement schedule management unit, 114b . . . conveying management unit, 114c . . . analysis operation management unit, 115 . . . storage unit, 116 . . . display unit, 117 . . . input unit, 118, 218 . . . reaction disk, 119, 219 . . . reagent disk, 120, 220 . . . reagent dispensing mechanism, 200 . . . sample rack conveying module, 300 . . . control device

The invention claimed is:

1. An automated analyzer comprising:
    a measurement unit configured to perform analysis;
    a circular and rotatable rack rotor having an axis of rotation and having a plurality of slots on which a respective sample rack, of a plurality of sample racks, is capable of being mounted;
    a first dispensing line and a second dispensing line, the first dispensing line extending away from the rack rotor in a first direction, the second dispensing line extending away from the rack rotor in a second direction that is opposite the first direction, wherein a virtual projection of the first dispensing line intersects with the axis of rotation of the rack rotor, wherein a virtual projection of the second dispensing line intersects with the axis of rotation of the rack rotor, wherein each of the first dispensing line and the second dispensing line is configured to load and unload a respective sample rack mounted with one or more sample containers, each sample container housing a respective sample for analysis from the rack rotor and to convey respective sample racks back and forth by a conveyor belt to a first dispensing position disposed on the first dispensing line and a second dispensing position disposed on the second dispensing line;
    a first dispensing mechanism disposed at the first dispensing position configured to dispense a respective sample from a respective sample container at the first dispensing position and a second dispensing mechanism disposed at the second dispensing position configured to dispense a respective sample from a respective sample container at the second dispensing position;
    a conveying line including a conveyor belt provided separately from the first dispensing line and the second dispensing line, extending in a third direction, which is different than the first direction and the second direction, and configured to convey a respective sample rack back and forth from a rack rotor end to another end of the conveying line by the conveyor belt;
    a first sample identification device and a second sample identification device; and
    a controller connected to the rack rotor, the first dispensing line, the first dispensing mechanism, the second dispensing line, the second dispensing mechanism, the conveying line, the first sample identification device and the second sample identification device,
    wherein a virtual projection of the conveying line intersects with the axis of rotation of the rack rotor and the conveying line is perpendicular to the first dispensing line and the second dispensing line,
    wherein each sample rack includes a sample identification medium,
    wherein the first dispensing line includes a first stopping position that is further away from the rack rotor than the first dispensing position,
    wherein the controller is programmed to:
    cause the first dispensing line to convey a first sample rack to be conveyed to the first dispensing position on the first dispensing line from a first slot on the rack rotor,
    determine whether the first sample rack is on the first dispensing line based on information read from the sample identification medium on the first sample rack by the second sample identification device,
    determine whether a second sample rack is on the convening line based on information read from the sample identification medium of the second sample rack by the first sample identification device,
    upon determining the second sample rack is on the convening line and the first sample rack is on the first dispensing line based on the information respectively read by the first sample identification device and the second sample identification device:
    cause the first dispensing line to convey the first sample rack to the first stopping position,
    cause the convening line to convey the second sample rack into the first slot on the rack rotor,
    rotate the rack rotor and cause the first dispensing line to convey the second sample rack to the first dispensing position on the first dispensing line while the first sample rack is maintained at the first stopping position, and
    cause the first dispensing mechanism to dispense a respective sample from the second sample rack at the first dispensing position.

2. The automated analyzer according to claim 1 further comprising:
    an urgent sample rack loading unit provided adjacent to the conveying line and configured to load the second sample rack;
    a sample rack supply unit provided adjacent to the conveying line and closer the rack rotor end of the conveying line than the urgent sample rack loading unit and configured to supply the first sample rack;
    a sample rack storage unit provided adjacent to the conveying line and closer to the rack rotor end of the conveying line than the sample rack supply unit and configured to store the first sample rack or the second sample rack; and an urgent sample rack wait portion of the conveying line, which is closer to the other end of the conveying line than the sample rack storage unit, wherein the control unit is configured to:

cause a third sample rack to wait in the urgent sample rack wait portion, cause the first dispensing line to convey the second sample rack in the first dispensing line into the first empty slot on the rack rotor, rotate the rack rotor and cause the conveying line to convey the second sample rack into the sample rack storage unit, and then cause the conveying line to mount the third sample rack into the first empty slot on the rack rotor.

* * * * *